United States Patent

Chen et al.

[11] Patent Number: 5,571,152
[45] Date of Patent: Nov. 5, 1996

[54] MICROMINIATURE ILLUMINATOR FOR ADMINISTERING PHOTODYNAMIC THERAPY

[75] Inventors: James C. Chen; Brian D. Swanson, both of Bellevue, Wash.

[73] Assignee: Light Sciences Limited Partnership, Bellevue, Wash.

[21] Appl. No.: 451,831

[22] Filed: May 26, 1995

[51] Int. Cl.⁶ ..................................................... A61N 1/30
[52] U.S. Cl. .................................. 607/92; 604/21; 606/14
[58] Field of Search .............................. 606/14, 15, 16, 606/17; 607/88, 89, 90, 92; 604/19, 20, 21

[56] References Cited

U.S. PATENT DOCUMENTS

| | | | |
|---|---|---|---|
| 3,785,383 | 1/1974 | Dotto | 607/90 |
| 4,336,809 | 6/1982 | Clark | 606/15 |
| 4,512,762 | 4/1985 | Spears | 604/21 |
| 5,445,608 | 8/1955 | Chen et al. | 604/20 |
| 5,474,528 | 12/1995 | Meserol | 607/88 |
| 5,489,279 | 2/1996 | Meserol | 607/88 |

OTHER PUBLICATIONS

G. Loeb, C. Zamin, J. Schulman, & P. Troyk, "Injectable microstimulator for functional electrical stimulation," North Sea: Transducers and electrodes, North Sea special feature, Nov. 1991, pp. NS13–NS19.

Y. Mitamura, E. Okamoto, A. Hirano, and T. Mikami, "Development of an Implantable Motor–Driven Assist Pump System," IEEE Transactions on Biomedical Engineering, vol. 37, No. 2, Feb. 1990, pp. 146–156.

*Primary Examiner*—Angela D. Sykes
*Assistant Examiner*—Eric F. Winakur
*Attorney, Agent, or Firm*—Ronald M. Anderson

[57] ABSTRACT

A plurality of microminiature light sources (10, 10') are injected at a treatment site to effect photodynamic therapy (PDT). Each of the microminiature light source beads includes an LED chip (12), a rectifier chip (14), and a plurality of electromagnetic receivers (18, 18') encapsulated within a biocompatible, light transmitting material such as silicone, forming a spherical bead that is only a few millimeters in diameter. The light source beads are sufficiently small so that they can be injected into a treatment site such as a tumor (46) from a syringe (58) through a needle (60). A photoreactive agent, which can serve as a carrier fluid for the microminiature light source beads, sensitizes the tissue at the treatment site so that light emitted by the LED chip when energized with an external electromagnetic transmitter (34) kills the tissue or other pathogens at the treatment site that have absorbed the photoreactive agent. Alternatively, a catheter (66) can be used for emplacing the microminiature light source beads at the treatment site.

29 Claims, 5 Drawing Sheets

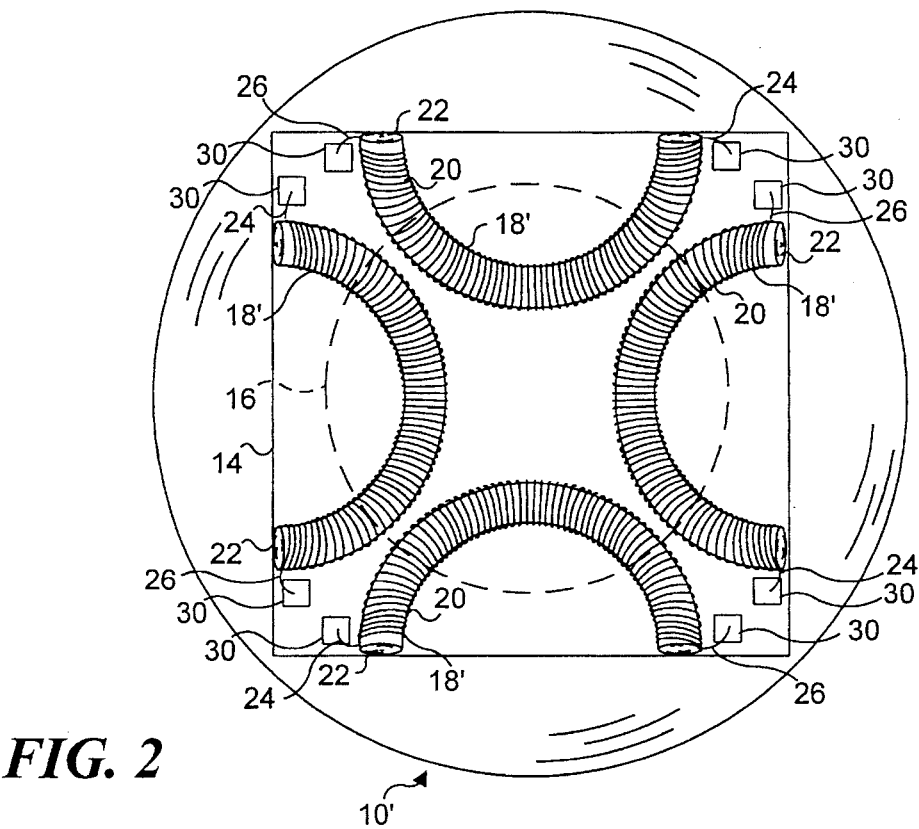
FIG. 2
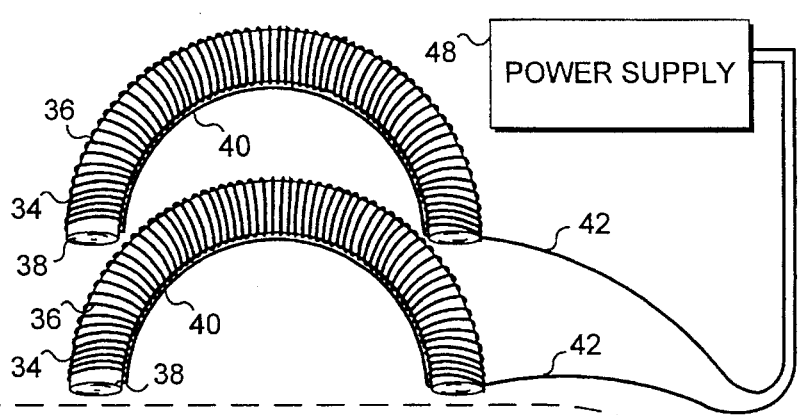
FIG. 4
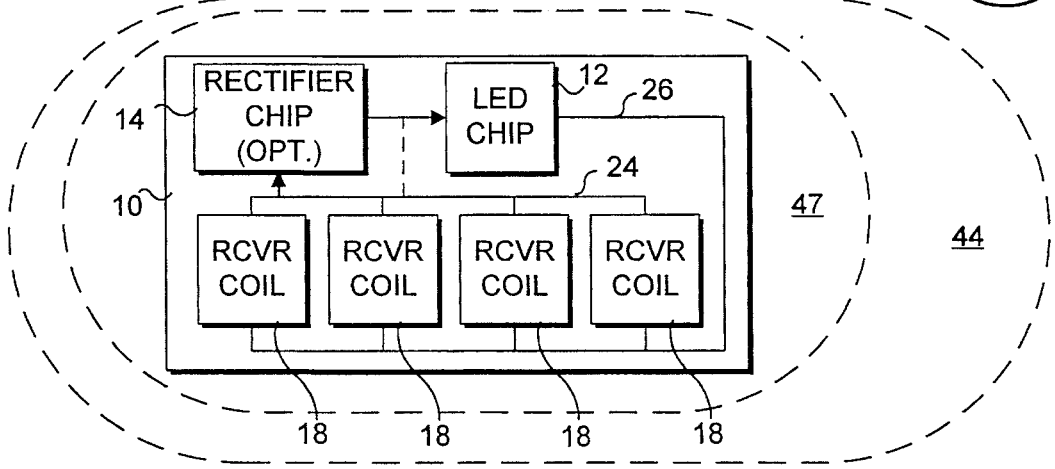

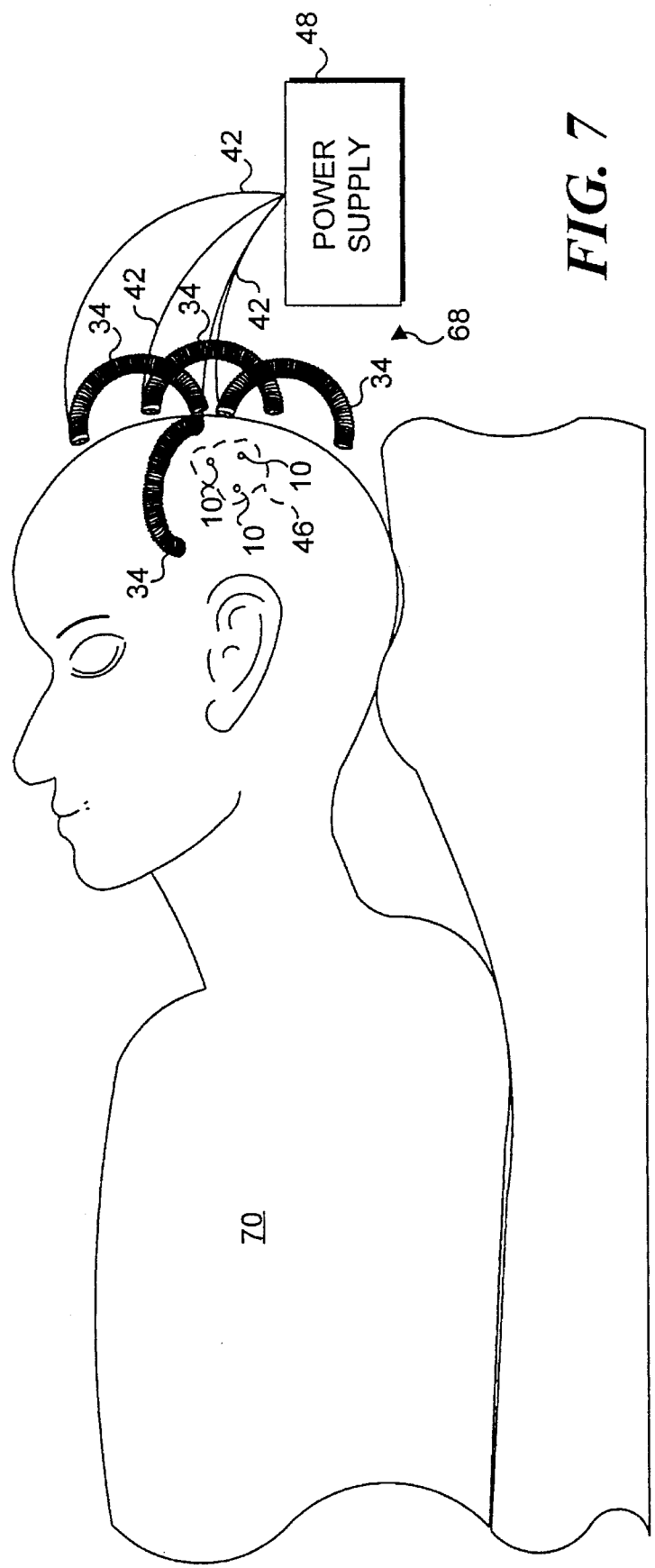

MICROMINIATURE ILLUMINATOR FOR ADMINISTERING PHOTODYNAMIC THERAPY

FIELD OF THE INVENTION

The present invention is generally directed to a light source for administering photodynamic therapy (PDT) and a method for providing such treatment, and more specifically, pertains to an invasively disposed light source energized from a power supply that is electromagnetically coupled to the light source and to a method for using such a light source to administer PDT.

BACKGROUND OF THE INVENTION

A tumor comprising abnormal cells is known to selectively absorb certain dyes perfused into the site to a much greater extent than surrounding tissue. For example, compared to normal cells, intracranial gliomas absorb up to a 28 times as much dye. Once pre-sensitized by dye tagging in this manner, the cancerous or abnormal cells can be destroyed by irradiation with light of an appropriate wavelength or waveband corresponding to an absorbing wavelength or waveband of the dye, with minimal damage to normal tissue. This procedure, which is known as PDT, has been clinically used to treat metastatic breast cancer, bladder cancer, lung carcinomas, esophageal cancer, basal cell carcinoma, malignant melanoma, ocular tumors, head and neck cancers, and other types of malignant tumors, and for destroying pathogens. Because PDT may be selective in destroying abnormal cells that have absorbed more of the dye, it can successfully be used to kill malignant tissue or organisms with less effect on surrounding benign tissue in the brain and other critical areas.

Typically, invasive applications of PDT have been used during surgical procedures employed to gain access to a treatment site inside the body of the patient. Relatively high intensity light sources have traditionally been used to reduce the duration of the treatment, and thus the time required for the surgery used to expose the treatment site, and because the majority of the prior art teaches that very high intensity light will more likely kill all of the malignant cells. Optical fibers in a hand-held probe are often used to deliver the intense light to the surgically exposed treatment site from a remote light source to reduce damage to surrounding tissue from the heat developed by the light source. High power lasers or solid-state laser diode (LD) arrays in a remote light source coupled to the optical fibers are normally used. A typical prior art light source for PDT would provide from about 0.10 watts to more than 1.0 watts of optical power to achieve the high intensity, short duration exposures that are preferred. Because of the relatively high light intensity and power required to achieve it, apparatus to provide PDT is often physically too large and too heavy to be readily moved about with the patient.

The theoretical basis behind PDT is that the light energy absorbed by dye molecules in the malignant cells is transferred to dissolved oxygen to produce a reactive species called "singlet oxygen." This highly reactive form of oxygen kills cancer cells, damages tumor vasculature, and can destroy viruses and bacteria. Since the concentration of dissolved oxygen in cells is comparatively low, it is possible that after all available oxygen is activated and/or reacted with the cell materials, any additional increase in light intensity will have a negligible incremental effect on the tumor or in killing malignant cells. The limiting factor on the rate of malignant cell death in PDT may well be the rate at which additional oxygen diffuses into the treatment site from surrounding tissue and through replenishment via the vascular system. Contrary to the teachings of most of the prior art, the effectiveness of each photon of light impacting the treatment area may be highest at very low light intensities, provided over extended treatment times, and the optical efficiency may in fact decrease with increasing exposure level.

Several researchers, including Haas et al., have shown that the level of cytotoxicity in PDT appears to be proportional to the product of the integrated light exposure and the photoreactive agent's concentration, rather than to the instantaneous light intensity. In other words, the degree of PDT response is dominated by the total amount of light absorbed by the photoreactive agent over the treatment period. It can therefore be argued that if: (a) the photoreactive agent's concentration in the target tissue is maintained at a therapeutic level, and (b) apparatus for delivering light of the proper wavelength or waveband to a treatment site over an extended period is available, then the benefits of PDT can be realized with a less aggressive and potentially less costly treatment carried out over a period ranging from days to weeks. Longer treatment periods at lower dosage rates may have other benefits as well, since high dosage rates continued over extended periods can result in adverse normal tissue response.

Maintenance of therapeutic photoreactive agent levels at a treatment site in the body is not difficult. It is well known that many PDT photoreactive agents have a long half-life in the human body. In some cases, however, it is necessary for a patient to avoid direct sunlight for up to 30 days to avoid sunburn or phototoxic side effects of the photoreactive agents that are infused into the body.

Teachings in the prior art have shown that it is possible, in certain cases, to obtain improved therapeutic results in PDT at a low light level. As reported by J. A. Parrish in "Photobiologic Consideration in Photoradiation Therapy," pp. 91–108, *Porphyrin Photosensitization*, Plenum Press, (1983), preliminary laboratory studies with hematoporphyrin and visible light suggest that the reciprocity effect does not always hold, and that low light intensity may be more effective in PDT, in an absolute sense. In these experiments, subcutaneous tumors in the flanks of newborn rats were treated with the same external dose of 620 nm radiation at intensities of 7.5, 28, and 75 mW/cm$^2$. At the same total light dosage, Parrish found that greater tumor necrosis occurred at the lowest light intensity used.

In addition, several researchers have shown that combinations of certain photoreactive agents and low light levels exhibit very potent cytotoxicity. For example, Nitzan et al. have shown that more than 99% of gram-positive *Staphylococcus aureus* and *Streptococcus faecalis* bacterial cultures can be killed with the application of 5 mW/cm$^2$ of broad band light from a tungsten bulb for 30 minutes, if the cultures are initially dosed with 1–10 micrograms/ml of deuteroporphyrin. Continued application of light for ten to eleven hours results in a sterile condition in the culture, i.e., no bacteria remain alive.

Labrousse and Satre have demonstrated a similar photodynamic extermination of amoebae when dosed with low concentrations of 4'5'-Diiodofluorescein isothiocyanate dextran and irradiated for about 30 minutes with broad band light of 8–10 mW/cm$^2$ from a tungsten lamp. Both of these experimental results are particularly significant because the fraction of a tungsten lamp's output energy that can be absorbed by either photoreactive agent is small, since each agent has a narrow absorbance waveband.

For all PDT light sources, the vast majority of the optical power delivered to tissue eventually degrades to heat. From a therapy perspective, it is likely that this heat load will augment the treatment due to improved chemical reaction rates at higher tissue temperatures. It is also true that cells kept above approximately 43° C. are not viable. This effect is, in fact, used in the treatment of cancer using hyperthermia. In that situation, an attempt is made to heat the target tumor with radio frequency (RF) energy to a temperature on the order of 43°–45° C., while maintaining surrounding healthy tissue below 43° C. Combining hyperthermia with conventional transcutaneous PDT has been shown by B. Henderson et al. to increase the efficacy of both treatments (see "Interaction of Photodynamic Therapy and Hyperthermia: Tumor Response and Cell Survival after Treatment of Mice in Vivo," *Cancer Research*, Vol. 45, 6071 (December 1985)). Combining hyperthermia treatment with PDT delivered, for example, by an implantable probe in accordance with the present invention, will very likely augment the effects of either treatment used alone in destroying tumors.

A wide range of therapeutic benefits may be realized with the apparatus and methods of the present invention, beyond destroying tumors. These benefits include, but are not limited to, the destruction of other abnormal cell types, the destruction of normal tissue for therapeutic ends, selective destruction of pathogenic microorganisms, viruses, and other self-replicating disease agents, treatment of vascular or hematologic disorders, reducing or controlling inflammation and the enhancement of normal cellular function, such as wound healing or immunologic response. It is contemplated that the PDT apparatus and method disclosed below can be applied to providing such therapeutic benefits in both plants and animals.

A method and apparatus for delivering light with an implantable probe, for extended periods of time, well beyond the duration that a treatment site within a patient's body can be exposed during surgery, is disclosed in U.S. Pat. No. 5,445,608 (Chen et al.). Several embodiments of an implantable probe suitable for this purpose are disclosed in the patent. All of the implantable probes disclosed therein include a plurality of light emitting diodes (LEDs) or LDs arranged in an array as the source of light administered to an internal treatment site. However, due to their size, a patient's body must be surgically opened in order to implant these probes at the treatment site, and then closed as the PDT proceeds. The probe thus emplaced provides light to the internal treatment site during the extended PDT.

Clearly, it would be desirable to be able to insert a light source at an internal treatment site to achieve the benefits of extended PDT at relatively low light levels, as taught by the above-referenced patent, without requiring that the treatment site be fully exposed through surgery. In many cases, surgery of this type to implant a relatively large probe may be traumatic to a patient, particularly if already weakened by the disease to be treated by PDT using the implantable probe. Further, to minimize infection and the discomfort involved with supplying electrical power to the implanted light source probe from an external power source through conductors that pass transcutaneously into the patient's body, it would be desirable to supply the electrical power without any such direct connection. In fact, the above-referenced patent teaches that power can be electromagnetically coupled from an external alternating current (AC) power supply to an implanted probe.

Inductive coupling of electrical power to implanted pace makers and other medical hardware from an external power supply is well known. Clearly, an implantable probe like those disclosed in the above-referenced patent is sufficiently large to include an electromagnetic transformer in which electrical current can be induced from an external power supply. However, the prior art does not teach or suggest a light source for administering PDT at an internal treatment site that is sufficiently small to be implanted without surgically exposing the treatment site. Further, the prior art does not teach how an implantable probe or light source of this type and size might be energized remotely, without requiring a direct connection to a power source. Conventional electromagnetic transformers used to inductively couple other types of medical hardware to an external power supply are much too bulky to accomplish this goal. The advantages of implanting a light source to administer PDT without subjecting the patient to the trauma of major surgery clearly indicate the utility of such an invention.

SUMMARY OF THE INVENTION

In accordance with the present invention, a microminiature light source for providing light to an internal treatment site to effect a PDT is defined. The light source comprises a light emitting device that produces light of a desired wavelength or waveband when energized by an electrical current, and the light emitting device includes a supporting substrate. A plurality of electromagnetic receivers are electrically connected to the light emitting device. Each electromagnetic receiver comprises a core and a plurality of turns of an electrical conductor wrapped around the core. The plurality of electromagnetic receivers are thus adapted to electromagnetically couple to an external electromagnetic transmitter. An electromagnetic field produced by the electromagnetic transmitter induces an electrical current to flow in the electromagnetic receivers. The electrical current applied to the light emitting device energizes it. A biocompatible, light transmitting material encloses the light emitting device and the plurality of electromagnetic receivers, forming a bead. The bead is adapted for insertion into the internal treatment site to administer the PDT by providing light of the desired wavelength or waveband.

The core of each of the plurality of electromagnetic receivers comprises a half toroid, comprising a metallic material selected for a characteristic high magnetic permeability and a low magnetic hysteresis. The half toroids are oriented in a different direction relative to each other to improve the coupling with the external electromagnetic transmitter, making the coupling less dependent upon the orientation of the bead when inserted at the treatment site.

The beads are generally spherical and preferably less than 5 mm in diameter. Also, the light emitting device preferably comprises a LED. Also included is a lens disposed to diffuse the light emitted by the light emitting device, thereby increasing the area of the treatment site that is illuminated.

Another aspect of the present invention is directed to a system for providing light of a desired wavelength or waveband to a treatment site disposed internally within a patient's body, to effect a photodynamic therapy of the treatment site. The system includes a light source that emits light of the desired wavelength or waveband when energized with an electrical current, and an electromagnetic receiver that includes a core around which is wrapped a plurality of turns of an electrical conductor. The electrical conductor is connected to the light source. A biocompatible, light transmitting sheath envelopes the light source and the electromagnetic receiver, forming a bead sized to pass through a tube. The tube is adapted to be inserted into a patient's body, for delivery of the bead and the light source contained therein to the treatment site. The system also includes a power supply that produces an AC voltage, and an electromagnetic transmitter that is connected to the power supply. When energized by the power supply, the electromagnetic transmitter is electromagnetically coupled to the electromagnetic receiver, thereby inducing an AC to flow in the electrical conductor wrapped around the core. The AC is used to energize the light source, producing light used to administer the PDT at the treatment site. Other elements of the system are consistent with those of the microminiature light source discussed above.

Yet another aspect of the invention defines the steps of a method for providing light of a desired wavelength or waveband to an internal treatment site to effect a photodynamic therapy. The steps of the method include providing a microminiature light source that emits light of the desired wavelength or waveband. The microminiature light source is encapsulated within a bead of a light transmissive, biocompatible material, and the bead encompasses an electromagnetic receiver. The bead is injected within the internal treatment site, and power is electromagnetically coupled to the electromagnetic receiver from an external power source, inducing an electrical current to flow in the electromagnetic receiver. The electrical current energizes the microminiature light source.

Other steps of the method are generally consistent with the functions performed by the elements of the system described above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 2 is a plan view of an alternative embodiment of the microminiature light source;

FIG. 4 is a block diagram of the components comprising a system that includes the microminiature light source;

Figure 6:
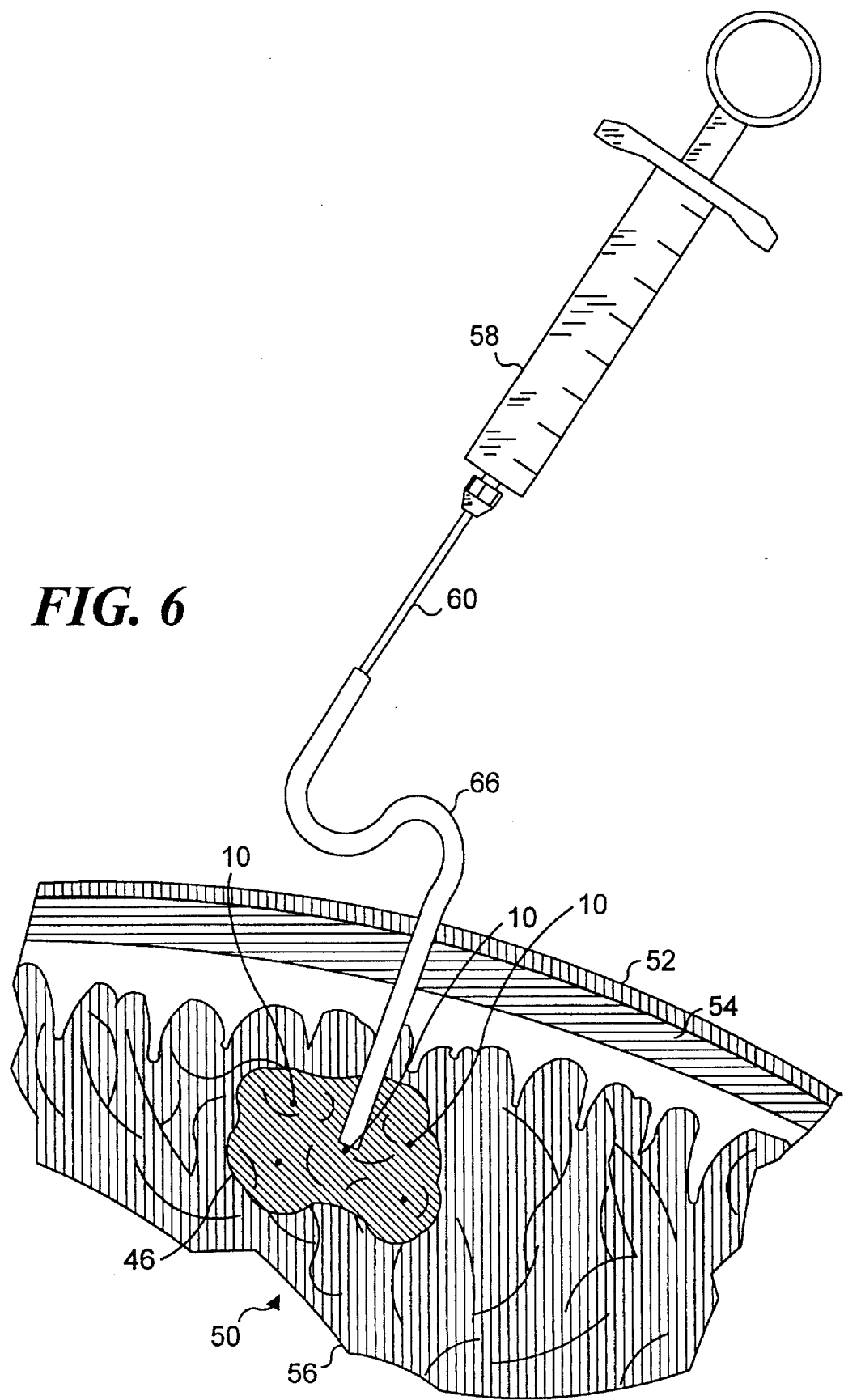

FIG. 6 is a cross-sectional view of a portion of a patient's skull, showing how a syringe and catheter are used to inject a plurality of microminiature light sources into a brain tumor; and FIG. 7 is side elevational view of a patient's upper torso, showing an array of electromagnetic transmitters used to couple power to a plurality of microminiature light sources that have been injected into a brain tumor.

DESCRIPTION OF THE PREFERRED EMBODIMENT

To minimize or eliminate the need to surgically expose an internal treatment site in order to implant a light source suitable for administering PDT over an extended time, the light source must be made smaller than any previously disclosed implantable light source. It should be noted that the present invention is directed to an implantable light source, i.e., to a source that is implanted within a treatment site and actually produces light that illuminates the treatment site. According, the present invention is not directed to a light source that is actually external to the treatment site, such as at the proximal end of an optical fiber, and does not include in the definition of light source as used herein, the distal end of such an optical fiber from which light is emitted to irradiate a treatment site in which the distal end of the optical fiber is disposed.

The prior art implantable light source probes for administering PDT have included a plurality of light sources organized in an array. Such probes are clearly too large to be transcutaneously disposed within an internal treatment site without first surgically incising and exposing the treatment site or creating a relatively large opening in the patient's body through which the probe can be inserted into the treatment site. In contrast, the present invention greatly reduces the size of the light source used to administer the PDT so that it can be readily inserted into a treatment site with only a minimal incision or in many cases, with no incision (other than a puncture) being required. Instead of using a plurality of light sources disposed in an array, as in the prior art implantable probes, the present invention preferably employs only a single source of light disposed in a microminiature, generally spherical form that is sufficiently small in diameter to be injected into the treatment site and remotely powered by an electromagnetic inductive coupling to an external power source.

Figure 1:
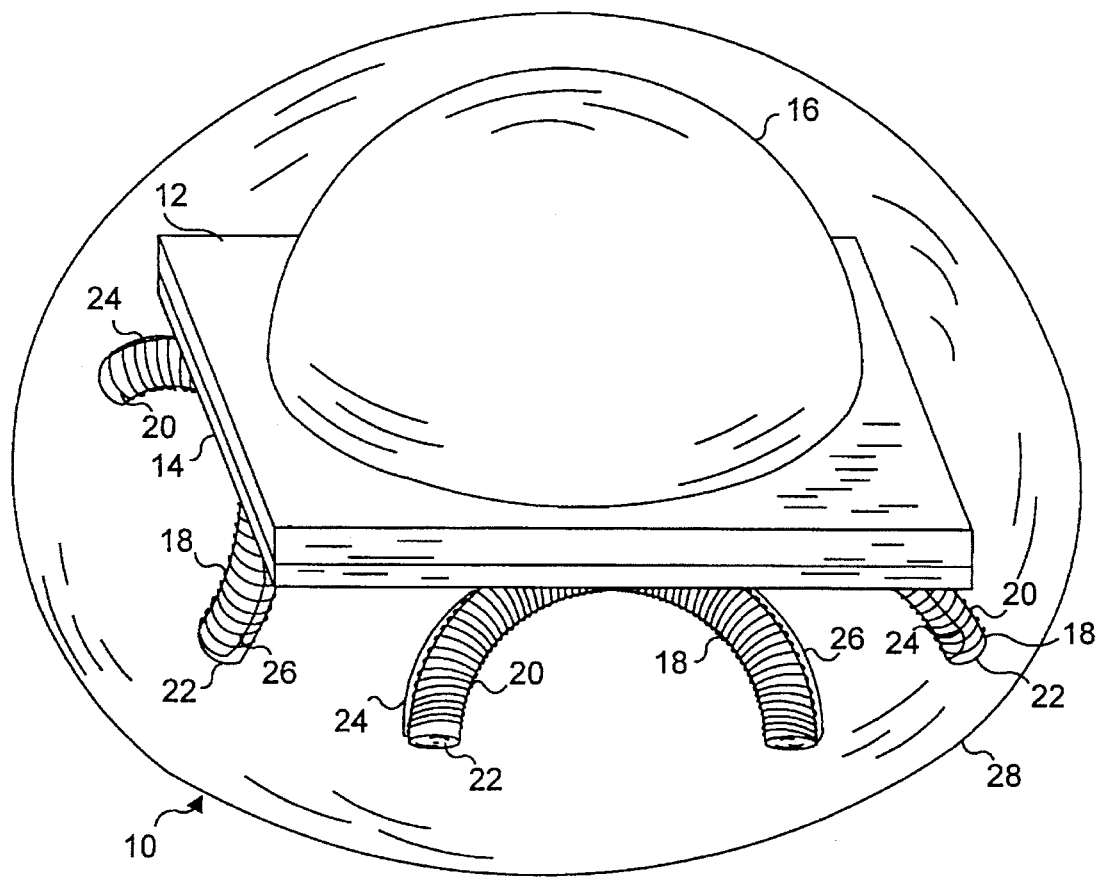
FIG. 1 is an isometric view of a microminiature light source that is encapsulated to form a bead.

Referring to FIG. 1, a first embodiment of a microminiature light source bead 10 in accordance with the present invention is illustrated. Light source bead 10 includes a single LED chip 12, which is mounted back-to-back with a rectifier chip 14 (optional). A diffusing lens 16 is disposed over the light emitting junction (not separately shown) of LED chip 12. Diffusing lens 16 diffuses the light produced by the LED junction and defocuses the light to increase the area of the treatment site. The light is thus emitted from light source bead 10 in approximately a hemispherical pattern. Preferably, the diameter of light source bead 10 is less than 5 min. A prototype of the light source bead has been produced having a diameter of about 5 mm. With further care in fabrication and perhaps as the techniques for microminiaturization improve, it is expected that the diameter of the light source bead can be substantially further reduced. Ideally, the beads should be as small as possible to permit them to be more readily injected within a treatment site.

Power must also be provided to energize the microminiature light source. Clearly, connecting the light source to an external power supply through an electrical conductor would be impractical and would defeat many of the advantages of the microminiature light source bead. Furthermore, providing an onboard battery supply would, with the current state of the technology, be impractical, due to the increased size and potentially harmful effects of any chemicals contained within the battery that might leak from the bead. Instead, the present invention includes means for remotely electromagnetically coupling power to energize the light source from an external AC power supply. Mounted under rectifier chip 14 are four electromagnetic receivers 18. Each electromagnetic receiver comprises a half-toroid core 22 about which is wrapped a plurality of turns of an electrical conductor 20. The electrical conductor used for this purpose must be very small in diameter, e.g., less than 30 gauge, in order to enable a sufficient number of turns of the conductor to be wrapped on the core to provide about 4 mA of DC required to energize the LED chip. More than 10 feet of electrical conductor were coiled on each of the half-toroid cores in the prototype device. Half-toroid cores 22 preferably comprise a ferrite material, which is suitable for producing an electromagnetic coil, due to its relatively high magnetic permeability and low magnetic hysteresis; however, other materials known to be suitable by those of ordinary skill in the art of producing electromagnetic coils can instead be used for this purpose.

Although the preferred embodiment shown in FIG. 1 includes only four electromagnetic receivers 18, it is contemplated that either fewer or more electromagnetic receivers may alternatively be included within the microminiature light source bead. In addition, it may be desirable to produce a microminiature light source bead that includes two light emitting devices mounted with the electromagnetic receivers disposed in between and so that light is emitted from both hemispheres of the light source bead. In this case, there would be no need to include optional rectifier chip 14, since one of the LED chips could be energized using the positive half cycles of the induced AC current, while the other LED chip is energized using the negative half cycles. A second embodiment microminiature light source bead 10' shown in FIG. 2 is more suitable for this modification, due to the flatter configuration of the electromagnetic receivers in that embodiment. The LED chips could more readily be mounted on opposite sides of the electromagnetic receivers.

For the first embodiment shown in FIG. 1, electromagnetic receivers 18 are mounted under rectifier chip 14 so that the horns or outwardly facing ends of half-toroid core 22 in each electromagnetic receiver are oriented in a different direction. As shown in this Figure, each electromagnetic receiver 18 is generally angled downwardly at approximately 45° relative to the under surface of rectifier chip 14, and is generally aligned with the four edges of the rectifier chip. The purpose of mounting the electromagnetic receivers so that they are oriented in different directions is to insure that the relatively random orientation of the light source bead after it is injected into a treatment site does not preclude electromagnetically coupling power to one or more of the electromagnetic receivers. If only a single electromagnetic receiver is provided on the microminiature bead, it may not be possible to induce sufficient electrical current within the electromagnetic receiver to energize LED chip 12. By including a plurality of the electromagnetic receivers oriented in different directions, at least one of the electromagnetic receivers should be oriented so that the horns of its core 22 are generally directed toward the nearest adjacent outer surface of the patient's body, thereby efficiently coupling power into the electromagnetic receiver.

During fabrication of the microminiature light source, each of the electromagnetic receivers is temporarily tacked in place on the undersurface of rectifier chip 14 with a suitable adhesive, and the coils of electrical conductor 20 are electrically connected (bonded) to pads (not shown in FIG. 1) disposed on the undersurface of the rectifier chip through leads 24 and 26. Thereafter, the assembly is potted, fully sealing it within a light transmissive, biocompatible material such as silicone, forming a spherical bead 28 that completely encloses and encapsulates LED chip 12, optional rectifier chip 14, diffusing lens 16, and the plurality of electromagnetic receivers 18. The microminiature size of light source bead 10 enables it to be implanted or injected at a treatment site within a patient's body using a minimal surgical technique, or with no surgery, as described below. Furthermore, a plurality of the microminiature light source beads can be implanted within the treatment site at various spaced-apart locations, enabling different portions of the treatment site that will receive PDT to be simultaneously illuminated at the spaced-apart locations with light produced by LED chip 12 in each of the microminiature light source beads.

In the second embodiment, light source bead 10' (shown in FIG. 2) includes four electromagnetic receivers 18' mounted flat against the undersurface of rectifier chip 14. Leads 24 and 26 electrically couple opposite ends of the electrical conductor 20 coiled around half-toroid core 22 in each electromagnetic receiver to pads 30, which are disposed on the undersurface of rectifier chip 14, adjacent its corners. Pads 30 are gold-plated, and leads 24 and 26 are bonded to the pads. In all other respects, microminiature light source bead 10' is identical to the first embodiment shown in FIG. 1.

Figure 3:
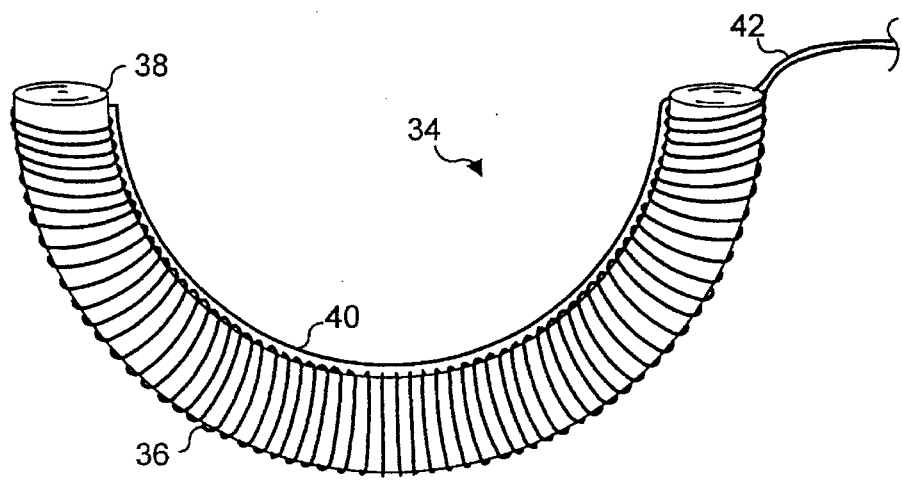
FIG. 3 is an elevational view of an electromagnetic transmitter that is used to couple power to the microminiature light source.

A preferred embodiment of an electromagnetic transmitter 34 is illustrated in FIG. 3. Electromagnetic transmitter 34 is a much larger version of the electromagnetic receivers used in the microminiature light source beads described above. The electromagnetic transmitter includes a half-toroid shaped ferrite core 38 around which is wrapped a plurality of turns of an electrical conductor 36. Other materials having high magnetic permeability and relatively how magnetic hysteresis can instead be used for the core, as will be apparent to those of ordinary skill in the art of building transformers and electromagnetic coils. Although not shown in FIG. 3, an insulating tape may be wrapped around the turns of electrical conductor 36, or the electromagnetic transmitter may be dipped in a resin to form a coating that stabilizes and fixes the turns of the electrical conductor on the core. A return lead 40 from one end of the electrical conductor comprises one of two leads 42 that are coupled to an AC power supply 48 (shown in FIG. 4).

Turning to FIG. 4, a block diagram illustrates how electrical power is preferably electromagnetically coupled from a plurality of electromagnetic transmitters 34 to the electromagnetic receivers within microminiature light source bead 10 or 10'. Although FIG. 4 shows only two electromagnetic transmitters 34 in use, it is likely that more than two will be used to insure that adequate power is coupled to the light source bead to energize the LED chip, since each additional electromagnetic transmitter used increases the power induced in the electromagnetic receivers. In FIG. 4, the microminiature light source bead is implanted at a treatment site 47, within a patient's body 44. Laboratory tests have confirmed that two or more electromagnetic transmitters 34 disposed adjacent the surface of the patient's body are able to noninvasively transtissue couple sufficient power to a plurality of electromagnetic receivers through from four to six centimeters of tissue to energize a single LED chip 12 with about 4 mA of current. AC power supply 48 is coupled to the electromagnetic transmitters, and in the preferred embodiment, provides an AC current to energize them, creating an electromagnetic field at an RF of about 70 KHz. The combined electromagnetic field produced by the plurality of electromagnetic transmitters 34 couples to one or more of the electromagnetic receivers 18 or 18', inducing a corresponding AC in the electromagnetic receivers at the same RF frequency. The plurality of electromagnetic receivers are connected in parallel with each other and in series with LED chip 12 and optional rectifier chip 14. Optional rectifier chip 14 is a full wave rectifier provided to insure that both the positive and negative cycles of the current wave form induced in electromagnetic receivers 18 or 18' are applied to energize LED chip 12. LED chip 12 only emits light when positive current flows through the junction of the chip from the anode to the cathode. Thus, unless full wave rectified DC is applied to the input of LED chip 12, it will only conduct during one half cycle of the induced current in the electromagnetic receiver(s). However, the rectifier chip is not required, since it is possible to induce sufficient current to operate the LED chip during only one half of each cycle, and at the radio frequency, the light output from LED chip 12 would be almost continuous.

Figure 5:
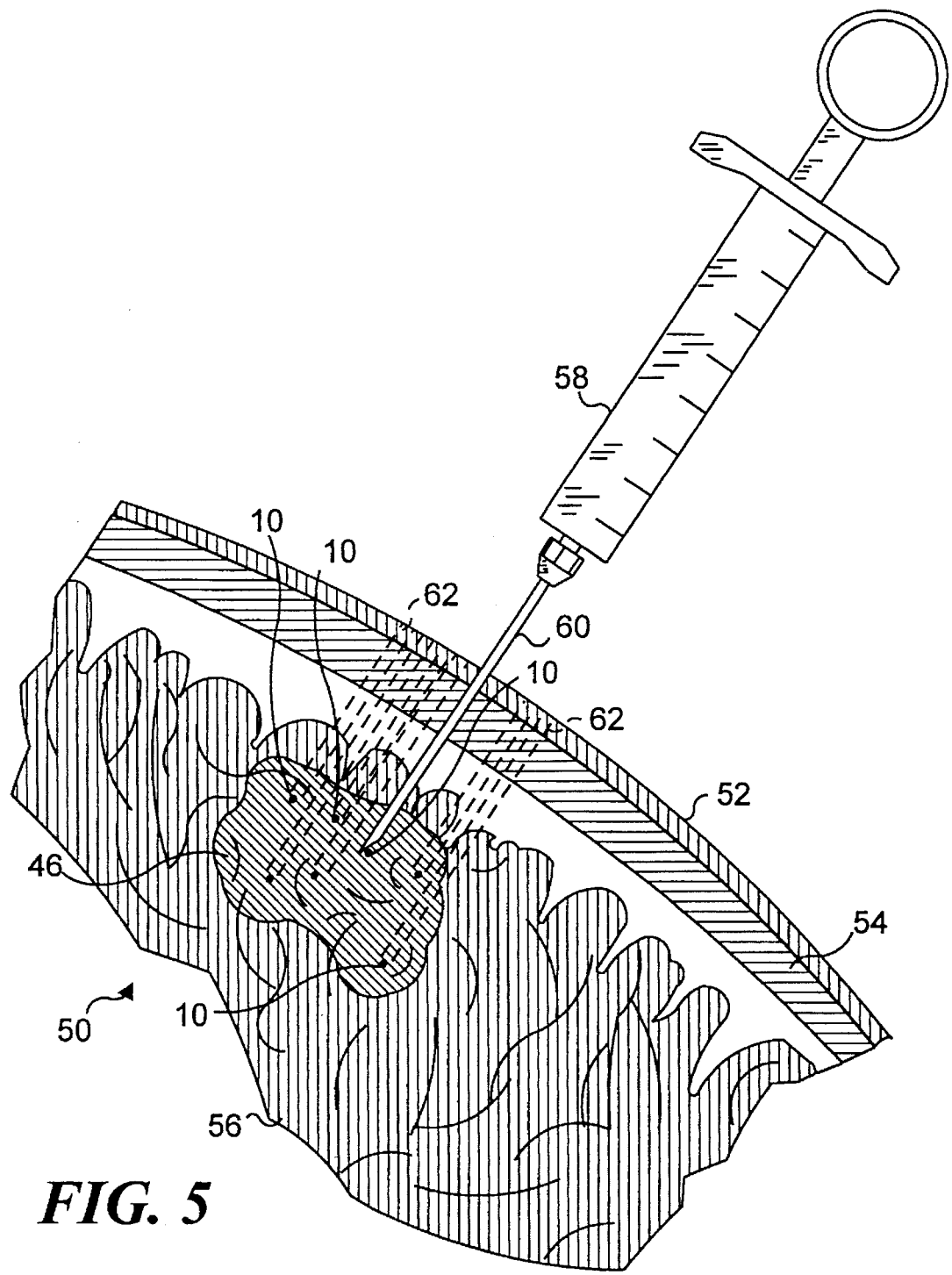
FIG. 5 is a cross-sectional view of a portion of a patient's skull, showing how a syringe and needle are used to inject a plurality of microminiature light sources into a brain tumor.

FIG. 5 is a sectional view 50 of a patient's brain 56, illustrating one technique for implanting microminiature light source beads 10 (or 10') within a brain tumor 46 using a syringe 58 and a needle 60. The microminiature light source beads are suspended within a suitable carrier fluid and drawn up into the syringe. Although the carrier fluid may be a saline solution, it can instead comprise a suitable PDT photoreactive agent for sensitizing tissue or organisms at the treatment site. Photoreactive agents that might be used for this purpose include: Phthalocyanines, Porphyrins, Ala, Chlorins, Purpurins, Pheophorbides, and Cationic Dyes. This list of photoreactive agents is provided merely to illustrate that many such substances are known that can be used in connection with the present invention. The photoreactive agent used will sensitize the tissue or organisms to be affected by the PDT at the treatment site. The absorption wavelength or waveband of the photoreactive agent employed will be approximately the same as the wavelength or waveband of light emitted by LED chip 12. For example, a photoreactive agent such as Pheophorbide a having a concentration of 5 micrograms/ml can be injected at the treatment site. An LED chip 12 should then be used that emits light having a wavelength of 660 nm, which is approximately the absorption wavelength of tissue that has been stained by this particular photoreactive agent.

Needle 60 is inserted through a small incision in a scalp 52 and then through an underlying hole drilled in skull 54. The needle passes through brain tissue 56 and into brain tumor 46. The photoreactive agent may be applied to the treatment site separately or may be used as the carrier fluid to convey the microminiature light source bead through needle 60 and into the brain tumor. When the LED chip within the bead is energized by inductively coupled power, malignant tissue at the treatment site that is sensitized by the photoreactive agent will be killed, thereby shrinking the brain tumor.

In the example shown in FIG. 5, brain tumor 46 is sufficiently large to require PDT at a plurality of points distributed throughout the tumor. Accordingly, a number of additional microminiature light source beads 10 are illustrated where emplaced by needle 60 and syringe 58 through a series of punctures 62 made by the needle after access to the brain tissue is achieved using a small diameter drill (not shown) to drill through the patient's skull. Since the microminiature light source beads are implanted within the brain tumor without requiring extensive surgery (only a small incision in the scalp and the small holes drilled in the skull), the trauma and other undesirable effects of fully invasive surgery on the patient are virtually eliminated.

Because the light emitted by each LED chip 12 within one of the beads is relatively low intensity, i.e., about 10 microwatts/cm$^2$, the PDT must be continued over an extended period of time, e.g., for at least 72 hours. However, as noted in the prior art patent referenced in the Background of the Invention, extended PDT at relatively low light levels has been found to be even more effective than PDT administered at high light levels for short periods of time. Accordingly, brain tumor 46 or other undesired tissue or pathogens at treatment sites in different portions of the body can readily be eliminated using the present invention.

FIG. 6 illustrates an alternative approach for implanting microminiature light source beads 10 within a brain tumor 46 (or within a different treatment site). In this alternative, a catheter 66 is introduced into the treatment site and serves as a passage through which the photoreactive agent and microminiature light bead can be injected into the site to carry out the PDT. One advantage of using a catheter is that the lumen within the catheter may be a larger diameter, enabling current generation microminiature beads that are about 5 mm in diameter to more easily be injected into a treatment site than through a smaller bore needle.

As illustrated in FIG. 7, it is preferable to position a plurality of electromagnetic transmitters 34 at different spaced-apart points around the treatment site to insure that sufficient power is induced in one or more of the electromagnetic receivers to energize the LED(s) within each of the microminiature light source beads. In this example, only four electromagnetic transmitters 34 are shown in an array 68 around brain tumor 46. The array surrounds the skull of a patient 70, who is shown in a reclining position. Not shown in the Figure are clamps or other devices used to stabilize the electromagnetic transmitters in the desired position. Since long-term exposure of tissue to the electromagnetic field produced by electromagnetic transmitters 34 may cause undesirable side effects, it is contemplated that from time to time, the electromagnetic transmitters will be moved to a different position so that the tissue between the ends of the half toroids comprising the electromagnetic transmitters will be positioned at different points around the patient's skull (or around other parts of a patient's body where the PDT is applied), thereby insuring that the tissue between the electromagnetic transmitter and the microminiature light source beads is subjected to the magnetic field for only a relatively short period of time compared to the duration of the PDT. Any harmful effects of a strong electromagnetic field on such tissue will thereby be minimized.

In addition to treating brain tumors, it is contemplated that the present invention can be used at almost any treatment site at which PDT may be implemented inside a patient's body. Using a needle or catheter to position the microminiature light source beads at the treatment site, it is possible to reach virtually any portion of the body without resorting to surgery to open up and fully expose the treatment site, to implant the light source required for PDT. It is also contemplated that the microminiature light source beads might be injected within a patient's bloodstream and allowed to circulate throughout the body, being energized only at a selected part of the circulatory system where the external electromagnetic transmitters are disposed adjacent the desired treatment site, or at predetermined points where the beads lodge due to their inability to pass through smaller capillaries. Since these light source beads are made of a biocompatible material, it is not necessary that they be extracted from the body once the PDT treatment is completed. Instead, they can be left in place without any harmful consequences to the patient.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A microminiature light source for providing light to an internal treatment site to effect a photodynamic therapy at said site, comprising:
   (a) a light emitting device that produces light of a desired wavelength or waveband when energized by an electrical current, said light emitting device including a supporting substrate;
   (b) a plurality of electromagnetic receivers electrically connected to the light emitting device, each one of the plurality of electromagnetic receivers comprising a core and a plurality of turns of an electrical conductor wrapped around the core, said plurality of electromagnetic receivers being thus adapted to electromagnetically couple with an external electromagnetic transmitter that produces an electromagnetic field to induce an electrical current to flow in the electromagnetic receivers, said electrical current being applied to the light emitting device to energize it; and
   (c) a biocompatible, light transmitting material that encloses the light emitting device and the plurality of electromagnetic receivers to form a bead, said bead being thus adapted for insertion into the internal treatment site to effect the photodynamic therapy by providing light to the treatment site.

2. The microminiature light source of claim 1, wherein the core of each of the plurality of electromagnetic receivers comprises a half toroid.

3. The microminiature light source of claim 2, wherein each of the half toroids is oriented in a different direction relative to each other to improve the coupling with the external electromagnetic transmitter, regardless of the orientation of the bead when inserted at the treatment site.

4. The microminiature light source of claim 1, wherein the core of each of the plurality of electromagnetic receivers comprises a metallic material selected for its high magnetic permeability and low magnetic hysteresis.

5. The microminiature light source of claim 1, wherein the bead is generally spherical and less than 5 mm in diameter.

6. The microminiature light source of claim 1, wherein the light emitting device comprises a LED.

7. The microminiature light source of claim 1, further comprising a lens disposed to diffuse the light emitted by the light emitting device.

8. A system for providing light of a desired wavelength or waveband to a treatment site disposed internally within a patient's body, to effect a photodynamic therapy of the treatment site, comprising:
   (a) a light source that emits light of the desired wavelength or waveband when energized with an electrical current;
   (b) an electromagnetic receiver that includes a core around which is wrapped a plurality of turns of an electrical conductor, said electrical conductor being connected to the light source;
   (c) a biocompatible, light transmitting sheath enveloping the light source and the electromagnetic receiver, forming a bead sized to pass through a tube, said tube being adapted to be inserted into a patient's body, for delivery of the bead and the light source contained therein to the treatment site;
   (d) a power supply that produces an alternating current voltage; and
   (e) an electromagnetic transmitter that is connected to the power supply and when energized by the power supply, is electromagnetically coupled to the electromagnetic receiver, thereby inducing an alternating current to flow in the electrical conductor wrapped around the core, said alternating current being used to energize the light source to provide light that effects the photodynamic therapy at the treatment site.

9. The system of claim 8, further comprising a rectifier that is connected to the electromagnetic receiver, said rectifier converting the alternating current to a direct current, which is supplied to energize the light source.

10. The system of claim 8, further comprising at least one other electromagnetic receiver that is connected to the light source, each of the electromagnetic receivers being oriented differently to improve electromagnetic coupling with the electromagnetic transmitter.

11. The system of claim 8, wherein the core of the electromagnetic receiver comprises a half toroid.

12. The system of claim 8, wherein the electromagnetic transmitter comprises a half-toroid core about which is wrapped a plurality of turns of an electrical conductor that is connected to the power supply.

13. The system of claim 8, further comprising an array of electromagnetic transmitters connected to the power supply, said electromagnetic transmitters being disposed at spaced-apart positions and at different orientations around the treatment site to improve electromagnetic coupling with the electromagnetic receiver.

14. The system of claim 13, wherein the electromagnetic transmitters comprising the array each include a half-toroid core, and opposite ends of the half-toroid core are oriented toward the treatment site.

15. The system of claim 8, wherein the tube comprises a needle that is connected to a syringe for injecting the bead encompassing the light source into the treatment site.

16. The system of claim 8, wherein the tube comprises a catheter having a distal end that is transcutaneously disposed at the treatment site.

17. The system of claim 8, further comprising a diffusing lens disposed within the bead, in a position overlying the light source, said diffusing lens diffusing the light emitted by the light source over the treatment site.

18. A method for providing light of a desired wavelength or waveband to an internal treatment site to effect a photodynamic therapy, comprising the steps of:
   (a) providing a microminiature light source that emits light of the desired wavelength or waveband, said microminiature light source being encapsulated within a bead of a light transmissive, biocompatible material, said bead encompassing an electromagnetic receiver;
   (b) injecting the bead within the internal treatment site; and
   (c) energizing the light source by electromagnetically coupling power to the electromagnetic receiver from an external power source to induce an electrical current to flow in the electromagnetic receiver.

19. The method of claim 18, wherein the step of electromagnetically coupling comprises the step of coupling the external power source to an electromagnetic transmitter that is externally disposed adjacent the treatment site.

20. The method of claim 19, further comprising the step of providing a plurality of electromagnetic transmitters coupled to the external power source, each of the plurality of electromagnetic transmitters comprising a half-toroid core having opposite ends that are oriented in different directions in an array about the internal treatment site.

21. The method of claim 20, further comprising the step of periodically moving the electromagnetic transmitter to minimize exposure of a portion of a patient's body that is disposed between the electromagnetic transmitters and the bead to an electromagnetic flux.

22. The method of claim 18, further comprising the step of providing a plurality of electromagnetic receivers within the bead, said plurality of electromagnetic receivers being disposed at different orientations within the bead to improve an efficiency of the electromagnetic coupling.

23. The method of claim 22, wherein each of the electromagnetic receivers includes a half-toroid core having opposed ends, the half-toroid core being wrapped with a plurality of turns of an electrical conductor, further comprising the step of positioning each half-toroid core so that its opposed ends face outwardly of the bead.

24. The method of claim 18, further comprising the step of diffusing the light emitted by the light source to increase an area of the treatment site receiving the light.

25. The method of claim 18, wherein the step of injecting comprises the steps of inserting a distal end of a needle that is connected to a syringe containing the bead into the treatment site, and forcing the bead from the syringe into the treatment site through the needle.

26. The method of claim 18, wherein the step of injecting comprises the steps of inserting a distal end of a catheter that is connected to a syringe containing the bead into the treatment site, and forcing the bead from the syringe into the treatment site through the catheter.

27. The method of claim 18, further comprising the step of injecting a plurality of beads into the treatment site at spaced-apart locations.

28. The method of claim 18, wherein the light source comprises an LED.

29. The method of claim 18, wherein the electrical current induced to flow in the electromagnetic receiver is an alternating current, further comprising the step of rectifying the alternating current to produce a direct current that is input to the light source to energize it.

* * * * *